(12) United States Patent
Kimball (10) Patent No.: US 7,827,005 B2
(45) Date of Patent: Nov. 2, 2010

(54) SYSTEM AND METHOD FOR TESTING HEAT EXCHANGE SYSTEM FOR HEAT EXCHANGE CATHETER

(75) Inventor: David Searl Kimball, Irvine, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 243 days.

(21) Appl. No.: 12/057,083

(22) Filed: Apr. 21, 2008

(65) Prior Publication Data

US 2009/0265113 A1   Oct. 22, 2009

(51) Int. Cl.
*G06F 11/30* (2006.01)

(52) U.S. Cl. .................................... 702/182

(58) Field of Classification Search ............... 702/32, 702/130, 131, 136, 176, 182, 183, 189, 193; 62/434

See application file for complete search history.

(56) References Cited

U.S. PATENT DOCUMENTS 6,581,403 B2 *   6/2003   Whitebook et al. ........... 62/434

\* cited by examiner

*Primary Examiner*—Mohamed Charioui
(74) *Attorney, Agent, or Firm*—John L. Rogitz (57) ABSTRACT

A heat exchange system for an indwelling catheter is tested for proper operation by observing whether a fluid temperature is within a command zone range and if not whether temperature moves toward the range or equalizes with it within predetermined parameters after a pump has stopped, and only if temperature exhibits none of the tested-for conditions indicating an error.

16 Claims, 7 Drawing Sheets

SYSTEM AND METHOD FOR TESTING HEAT EXCHANGE SYSTEM FOR HEAT EXCHANGE CATHETER

FIELD OF THE INVENTION

The present invention relates generally to systems and methods for effecting non-standard fluid line connections.

BACKGROUND OF THE INVENTION

It has been discovered that the medical outcome for a patient suffering from severe brain trauma or from isehemia caused by stroke or heart attack is improved if the patient is cooled below normal body temperature (37.degree. C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present invention, the above-mentioned advantages in regulating temperature can be realized by cooling or heating the patient's entire body. Moreover, the present invention understands that since many patients already are intubated with central venous catheters for other clinically approved purposes anyway such as drug delivery and blood monitoring, providing a central venous catheter that can also cool or heat the blood requires no additional surgical procedures for those patients. However, single purpose heat exchange catheters such as are made by Innercool Therapies of San Diego, Calif. and Zoll Medical Corp. can also be less optimally used.

Regardless of the particular catheter used, it is clear that heat must be removed from or added to the coolant that flows through the catheter. As still further understood by the present invention, it is desirable that the heat exchange system be easy to use by health care personnel, and provide for monitoring systems and convenient temperature control. U.S. Pat. No. 6,146,411, incorporated herein by reference, discloses one such heat exchange system.

As understood herein, it would be advantageous to test the heating/cooling system to ensure proper functionality regarding the ability of the system to cool or heat the glycol liquid that in turn will heat or cool the saline liquid being used in the catheter.

SUMMARY OF THE INVENTION

A computer-implemented method for testing for proper functioning of a heat exchange system engageable with an indwelling heat exchange catheter to circulate working fluid therein using a pump includes determining whether temperature of heat exchange fluid in a chamber through which the working fluid is circulated is within a range of a target temperature. If the temperature of the heat exchange fluid is not within the range, the method includes stopping the pump. Only if (1) the temperature is not within the range at the elapse of the predetermined period, or (2) the temperature has not changed during the predetermined period by at least a predetermined amount, is an error indication returned.

If it is determined that the temperature is not within the range, the method may include deciding whether the temperature is warmer than the range or cooler than the range. If the temperature is warmer than the range the method can further include measuring the temperature with the pump stopped during the predetermined period and returning an error only at the elapse of the predetermined period if the temperature is not within the range or if the temperature has not changed during the predetermined period by at least the predetermined amount. On the other hand, if the temperature is cooler than the range the method can further include measuring the temperature with the pump stopped during the predetermined period and, if the temperature has not changed by the predetermined amount since the pump was stopped, determining whether a compressor has started. The test can be delayed if the compressor has not started.

In another aspect, a heat exchanger for treating working fluid to be circulated through an indwelling heat exchange catheter includes a pump for pumping the working fluid in a fluid path, and a heat exchange chamber in the path and containing a heat exchange fluid having a temperature. A processor controls the pump. The processor executes logic that includes determining that the beat exchanger is not working properly if the temperature of the heat exchange fluid is not within an expected range only if (1) substantial equalization of heat exchange fluid temperature with working fluid temperature does not occur within a predetermined period after stopping the pump, or (2) temperature does not change by at least a predetermined amount within a predetermined period after stopping the pump.

In still another aspect, a processor for a heat exchange system for heating and cooling a working fluid circulated through a catheter by a pump is programmed to determine whether a fluid temperature is within a command zone range and if not, to determine whether temperature moves toward the range or equalizes with it within predetermined parameters after a pump has stopped. Only if temperature does not move toward the range or equalize with it within predetermined parameters after the pump has stopped does the processor indicate an error.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
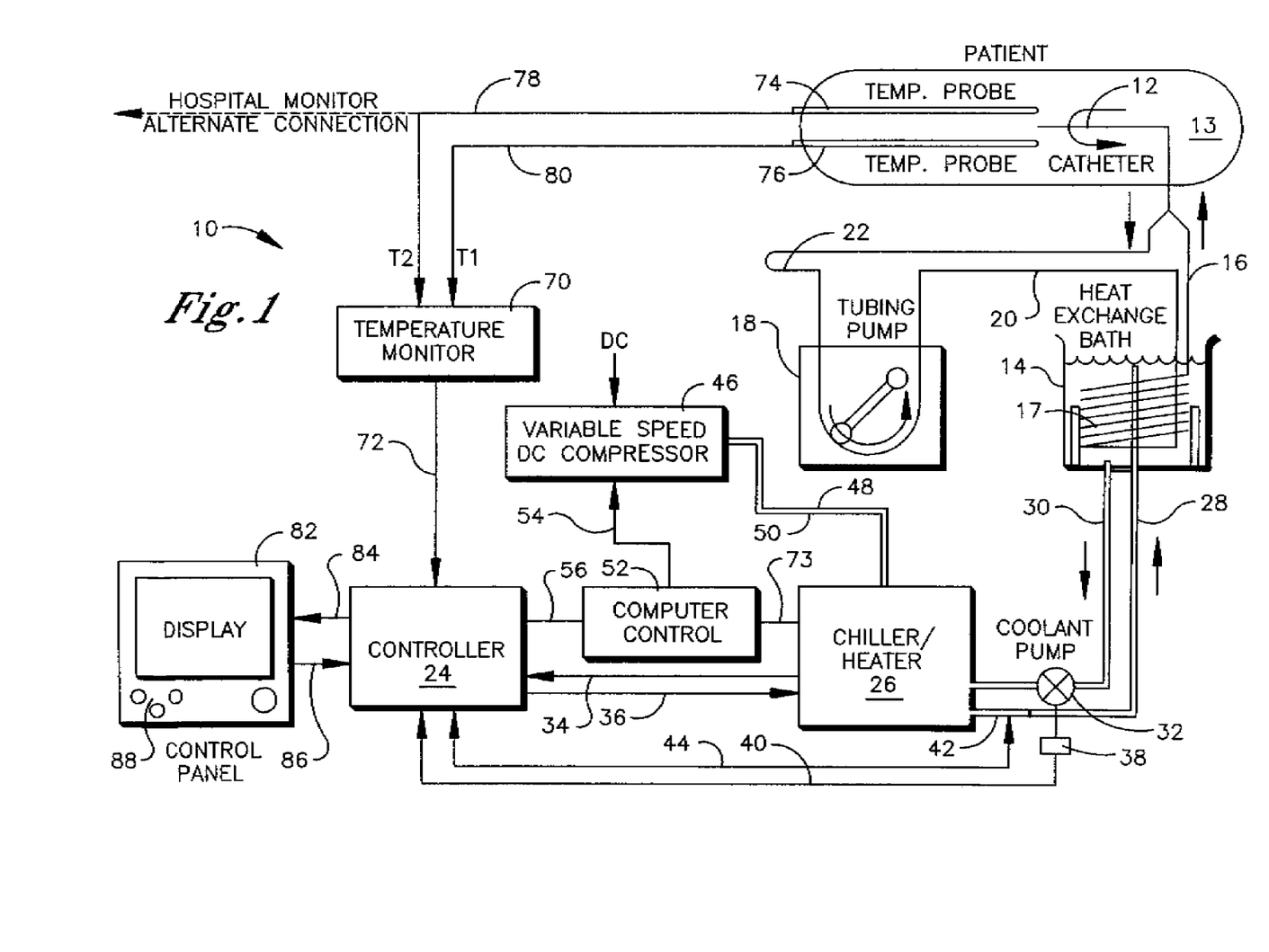
FIG. 1 is a block diagram of an example system in accordance with present principles.

Referring initially to FIG. 1, a patient heating/cooling system is shown and generally designated 10. As shown, the system 10 includes three separate fluid circuits: a saline circuit (also referred to as the working fluid circuit), a water glycol circuit (also referred to as the heating/cooling fluid circuit), and a refrigerant circuit (also referred to as the refrigerating fluid circuit.)

Taking the saline circuit first, an indwelling heat exchange catheter 12 that can be inserted into a patient 13 during an operation is connected to a heat exchange bath 14 by a saline supply line 16. The supply line 16 is connected to a coiled or helical heat exchange tube 17 that is immersed in the bath 14 fluid to exchange heat therewith. In turn, the heat exchange tube 17 is connected to a peristaltic tubing saline pump 18 by fluid line 20.

It is to be understood that in a preferred embodiment, the saline pump 18 has three modes: a standby or off mode, a treatment mode, and an idle mode wherein the saline pump 18 operates very slowly, but does not stop. In the idle mode, the patient 13 is effectively thermally decoupled from the heating/cooling system 10.

As further shown in FIG. 1, a saline return line 22 communicates saline from the catheter 12 to the saline pump 18 to complete the saline circuit. It is to be appreciated that the tubes 16, 17, 20, and 22 can be provided as a disposable IV tubing set.

FIG. 1 also shows a system controller 24. As described in further detail below, the system controller 24 receives signals from a saline level detector (not shown) regarding the level of saline therein and uses this information to control the saline pump 18.

It is to be understood that within the saline circuit, saline is circulated to and from the catheter 12 through the helical heat exchange tube 17 in the heat exchange bath 14. As described in detail below, the heat exchange bath 14 is filled with heating/cooling fluid, preferably water glycol. The water glycol can be heated or cooled in order to heat or cool the saline and thus, increase or decrease the temperature of the patient 13 into which the catheter 12 is inserted. Also, it is to be understood that the preferred working fluid is saline, but any similar fluid well known in the art can be used.

Now considering the water glycol circuit, the water glycol circuit communicates with a chiller/heater 26 via a water glycol supply line 28 and a water glycol return line 30. A water glycol pump 32 is installed in the water glycol return line 30 to circulate water glycol through the water glycol circuit.

Further, the system controller 24 is connected to the chiller/heater 26 via electrical lines 34 and 36. Moreover, the system controller 24 is connected to a safety switch 38 at the water glycol pump 32 via electrical line 40. Thus, the system controller 24 can control the operation of the chiller/heater 26 based on signals from a temperature monitor, described below, and control the operation of the water glycol pump 32 based on level signals from infrared detectors (not shown) that are disposed within a water glycol level detector (not shown).

The system controller 24 is also connected to a temperature sensor 42 via electrical line 44 placed at the outlet of the chiller/heater 26. The controller 24 uses input from the temperature sensor 42 to control the chiller/heater 26 and other system 10 components.

In one non-limiting embodiment, the water glycol may be pumped through the water/glycol circuit the chiller/heater 26 can heat or cool the water glycol. Within the heat exchange bath 14, the water glycol exchanges heat with the saline. Thus, the water glycol can be used to heat or cool saline and in turn, heat or cool the patient in which the catheter 12 is intubated. It is to be further understood that water glycol is the preferred heating/cooling fluid. However, any other fluid with similar properties can be used.

Now considering the third (refrigerant) circuit, a compressor 46, which in non-limiting implementations may be a variable speed DC compressor, is in fluid communication with the chiller/heater 26 via a refrigerant supply line 48 and a refrigerant return line 50. It is to be understood that the compressor 46 is filled with refrigerant, e.g., R134a. A compressor controller 52 is connected to the compressor 46 via an electrical line 54. In turn, the system controller 24 is connected to the compressor controller 52 via electrical line 56. The compressor controller 52 is also connected to a heater, described below, within the chiller/heater 26 via electrical line 73.

It is to be understood that the system controller 24 receives temperature signals from the temperature monitor, described below, and uses these signals to control the operation of the compressor 46 and the heater. The compressor 46 is used to compress refrigerant which, when it expands in the chiller/heater 26, cools the water glycol that is pumped through the chiller/heater 26 by the water glycol pump 32.

As further shown in FIG. 1, a temperature monitor 70 is connected to the system controller 24 via an electrical line 72. A first patient temperature probe 74 and a second patient temperature probe 76 preferably are connected to the temperature monitor 70 via electrical lines 78 and 80, respectively. As intended herein, the temperature monitor 70 uses the temperature probes 74 and 76 to monitor the temperature of the patient 13. Moreover, the temperature monitor 70 sends signals to the system controller 24 representing the temperature of the patient 13. These signals are used by the system controller 24 to control the operation of the chiller/heater 26, the saline pump 18, and the compressor 46.

FIG. 1 shows a display device 82 that is connected to the system controller 24 via electrical line 84 and electrical line 86. Preferably, the display device 82 provides a visual indication of the patient's temperature and the bath temperature. For example, the display device 82 can be used to output graphs of minute by minute patient temperature (for, e.g., twenty one days) and water glycol bath temperature. The display device 82 can also be used to provide information regarding the cooling power required by the patient, whether the system is heating or cooling the bath, and at which rate, e.g., low, medium, or maximum, the system is heating or cooling the bath. Further, the display device 82 can display the current patient temperature and the patient target temperature.

It is to be understood that a user can scroll the graphs left or right with respect to a stationary cursor within the center of the display. As the graphs are scrolled, information corresponding thereto can be displayed. As shown, the display device 82 also includes a control panel 88 to allow a user, i.e., a doctor or a nurse, to input data, such as a target patient temperature, to the system 10.

Figure 2:
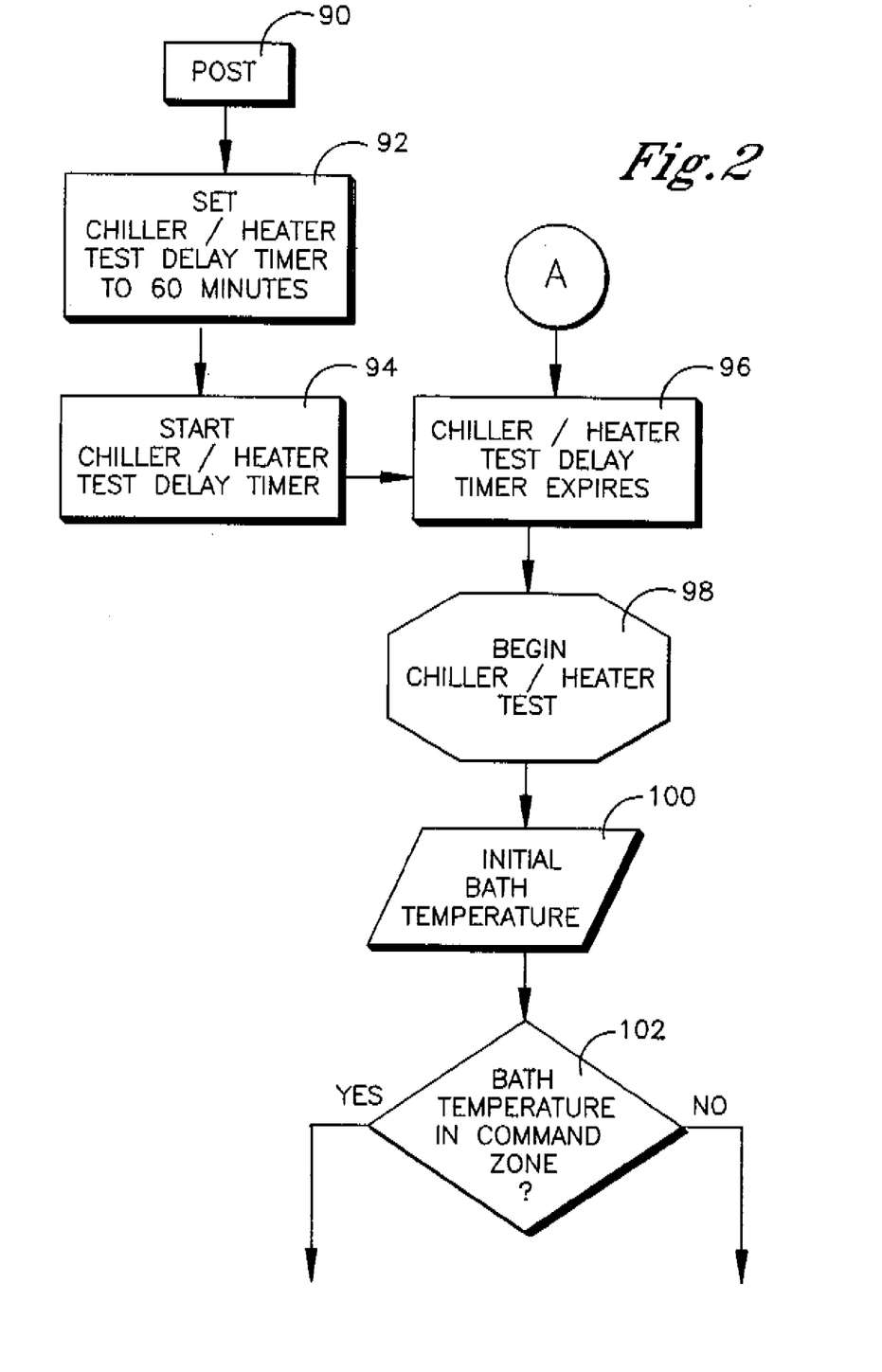
FIGS. 2 and 3 are flow charts showing example logic in accordance with present principles.

Now referencing FIG. 2, the beginning of the logic for testing the chiller/heater 26 of testing a cooling/heating system is shown, though it is understood that the present invention is not to be limited to only the current system.

Beginning with block 90 and before the catheter system engaged with a patient, a "power on self test" (POST) occurs. During the POST, an initial test is performed to ensure that certain basic features of the system 10 which are not central to present principles are functioning properly. Assuming the POST test passes, the catheter system is engaged with the patient. The logic next moves to block 92. At block 92 a chiller/heater 26 test timer is set to a specified time interval from which it will count down. In one non-limiting implementation, the time interval can be sixty minutes, but a different time interval may be used. Then at block 94 the chiller/heater 26 test timer begins to count down.

At block 96 the chiller/heater 26 test timer expires. Block 96 hereinafter begins a logic subseries generally designated as Logic Flow A. The expiration of the timer indicates that a test of the functionality of the chiller/heater 26 should be performed.

At block 98 the chiller/heater 26 test begins. The chiller/heater 26 test determines whether the chiller/heater 26, which cools glycol used in the heat exchange bath 14, is properly functioning as follows.

At block 100 the logic determines the initial heat exchange bath 14 temperature. The logic then determines at diamond 102 whether the heat exchange bath 14 temperature determined at block 100 is within the intended temperature range, hereafter designated as the "Command Zone." In one embodiment, the Command Zone can be a temperature range from one degree Celsius below commanded bath temperature to one degree above commanded bath temperature, although other ranges may be used.

If the heat exchange bath 14 temperature is within the Command Zone, the logic then moves to block 104 where another chiller/heater 26 test timer is set to count down. This time interval is preferably less than the first time interval determined at block 92, preferably but not limited to a fifteen minute interval.

By determining that the heat exchange bath 14 temperature is within the Command Zone, the logic may conclude that the chiller/heater 26 is functioning properly. Then at block 106 the timer begins another countdown and the logic then reverts back to the beginning of Logic Flow A.

Referring back to diamond 102, should the logic determine that the heat exchange bath 14 temperature is not within the Command Zone, the logic then moves to block 108 where the chiller/heater 26 test timer is set to a specified time interval that may if desired be substantially similar to the interval used at block 92.

Then at block 110 the chiller/heater 26 test timer begins to count down from the given time interval. The bath 14 temperature may not have been within the Command Zone when the initial bath temp 100 was determined. Thus the timer that begins at block 110 provides an opportunity for the chiller/heater 26 to beat or cool the glycol used in the heat exchange bath 14 so that the temperature of the bath 14 reaches the Command Zone.

At block 112 the chiller/heater 26 test timer expires and the logic moves to block 114, where the coolant pump 18 is stopped. Moving to decision diamond 116, the logic determines whether the heat exchange bath 14 temperature is above the Command Zone.

Figure 3:
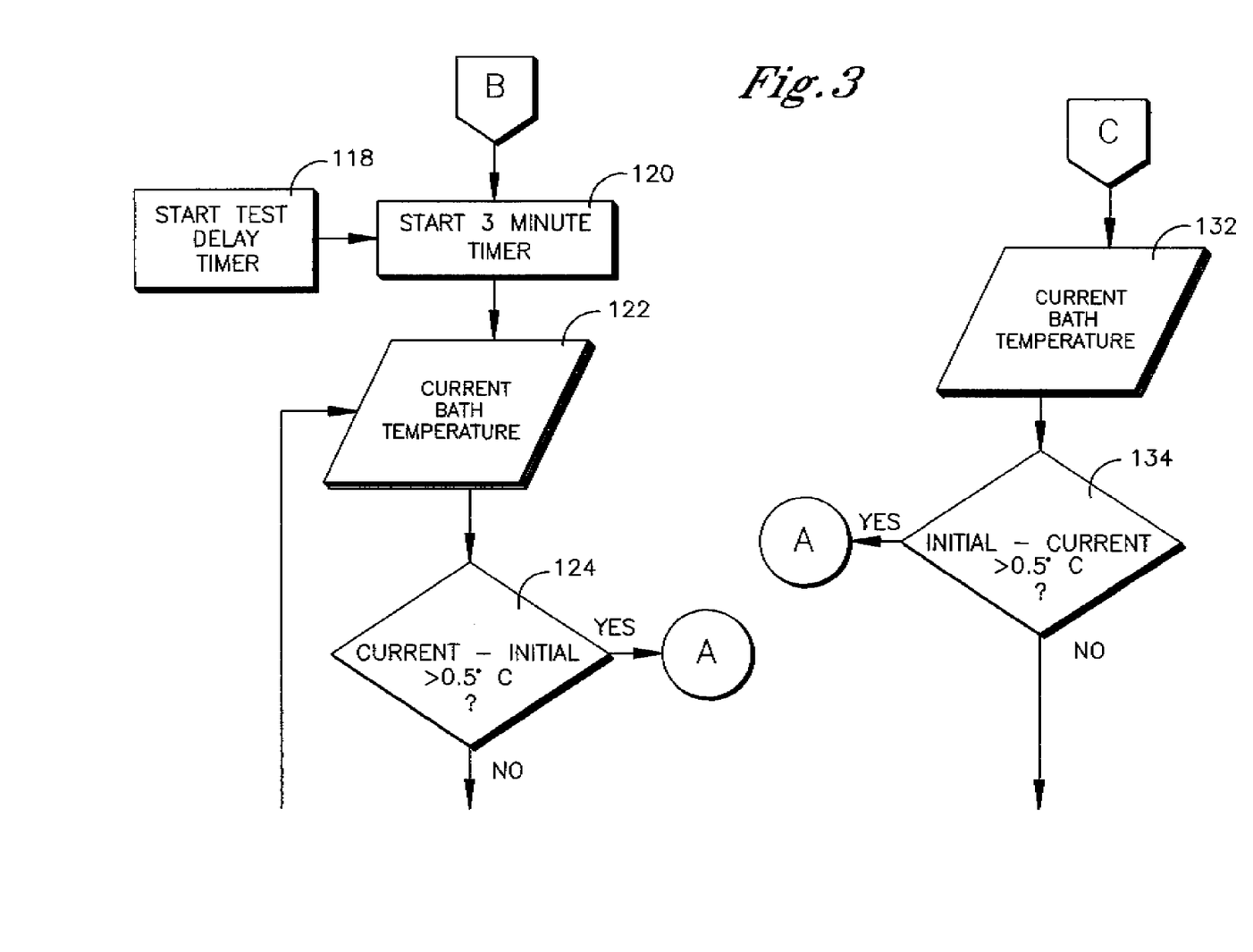

If the heat exchange bath 14 temperature is not above the Command Zone, the logic moves to Logic Flow B which is referenced in FIG. 3. If the heat exchange bath 14 temperature is above the Command Zone, the logic instead diverts to Logic Flow C, also referenced in FIG. 3.

First assuming that the temperature is not above the Command Zone, reference is now made to Logic Flow B in FIG. 3. At block 118 a chiller/heater 26 timer is set to a specified period of time, preferably but not limited to three minutes. At block 120 the chiller/heater 26 test timer begins. During the expiration of the timer that began at block 120, the coolant pump 18 that was stopped at block 114 remains stopped. With the pump 18 stopped, the chiller/heater 26 is able to reach the targeted Command Zone in the bath 14 more quickly since no heat transfer takes place in the bath when the pump is stopped.

Moving to block 122, the logic determines the current bath 14 temperature. Then at diamond 124, the logic subtracts the current temperature from the temperature at which the bath was when the pump was stopped at block 114, as measured at state 116 in FIG. 2. Remaining at diamond 124, the logic takes the current bath 14 temperature and subtracts the initial temperature. The logic then determines whether the difference between the current and initial temperature is greater than a threshold, which in one non-limiting embodiment may be half a degree Celsius.

If at decision diamond 124 the logic determines that the difference in temperature is greater than half a degree Celsius, the logic reverts back to the beginning of Logic Flow A, meaning that the system test has passed in that the system is attempting to regain the command zone at an acceptably fast rate of temperature change. That is, if the difference is greater than half a degree Celsius, this indicates that the chiller/heater 26 is functioning properly.

However, if it is determined that the temperature of the bath has changed less than the threshold (e.g., less than one-half of one degree) during the period in which the pump is stopped, the logic then continues to decision diamond 126, wherein the logic determines whether the current heat exchange bath 14 temperature is within the Command Zone range. If the logic determines that the current temperature is within the Command Zone, the logic reverts back to the beginning of Logic Flow A.

On the other hand, if the logic determines that the current temperature is not within the Command Zone, the logic continues to decision diamond 128. At diamond 128 the logic determines whether the chiller/heater 26 test timer has expired. If it has not expired, the logic reverts back to block 122 where the logic executes the same process until the timer that began at block 120 expires.

In contrast, if the timer has expired while the bath 14 temperature is neither within the Command Zone or heated at least a predetermined amount, an error is returned at block 130. The error, which may be indicated aurally or visually on, e+g., the display device 82, is reported because, after the relatively short timer period (three minutes being an example time), the system bath 14 temperature should have either reached the Command Zone or heated at least half a degree Celsius. If it has not, then the chiller/heater 26 is not functioning properly and an error is reported.

Now reverting back to diamond 116 and assuming that the temperature is above the Command Zone, reference is made to Logic Flow C in FIG. 3. At block 132, the logic determines the current bath 14 temperature.

Moving to diamond 134, the logic subtracts the initial temperature from the current temperature determined at block 132. Remaining at diamond 134, the logic takes the number just determined by subtracting the current temperature from the initial temperature and determines whether the difference is greater than a predetermined temperature change, e.g., half a degree Celsius.

If at decision diamond 134 it is determined that the difference in temperature is greater than half a degree Celsius, the logic reverts back to the beginning of Logic Flow A. A difference in temperature that is greater than half a degree Celsius indicates that the chiller/heater 26 is functioning properly and cooling the bath 1.4 temperature to bring it to within the Command Zone.

However, if it is determined that the difference in temperature is less than half a degree Celsius, the logic then continues to decision diamond 136. At diamond 136, the logic determines whether the current heat exchange bath temperature is within the Command Zone. If the logic determines that the current temperature has already been brought to within the Command Zone, the logic reverts back to the beginning of Logic Flow A.

If the logic determines that the current temperature is still not within the Command Zone, however, the logic continues again to diamond 138. At diamond 138 the logic determines whether the compressor 46 has started. If the compressor 46 has started, it should be cooling the glycol being pumped to the bath 14. However, if the compressor 46 has not started, the logic reverts back to the beginning of Logic Flow C and proceeds again. The logic is thus waiting for the compressor 46 to start.

If the logic determines that the compressor 46 has started, the logic may proceed to block 140. At block 140, a chiller/heater 26 test delay timer is set to a short period of time, preferably but not limited to three minutes. At block 142 the chiller/heater 26 test delay timer begins.

At the expiration of the delay the logic then moves to block 144 where the logic determines the current bath 14 temperature. Moving to diamond 146, the logic subtracts the initial temperature determined at block 100 from the current temperature determined at block 144. Remaining at diamond 146, the logic takes the number just determined by subtracting the current temperature from the initial temperature and determines whether the difference is greater than half a degree Celsius.

If at decision diamond 146 it is determined that the difference in temperature is greater than a predetermined delta, e.g., half a degree Celsius, the logic reverts back to the beginning of Logic Flow A. A difference in temperature that is greater than the predetermined delta indicates that the chiller/heater 26 is functioning properly.

However, if it is determined that the difference in temperature is less than the predetermined delta, the logic then continues to decision diamond 148. At diamond 148, the logic determines whether the current heat exchange bath 14 temperature is within the Command Zone. If the logic determines that the current temperature is already within the Command Zone, the logic reverts back to the beginning of Logic Flow A.

However, if the logic determines that the current temperature is still not within the Command Zone, the logic continues again to decision diamond 150. At diamond 150, the logic determines whether the chiller/heater 26 test timer has expired. If it has not expired, the logic reverts back to block 144 where the logic executes the same process.

However, if the timer has expired while the bath 14 temperature is neither within the Command Zone or cooled to at least half a degree Celsius, an error is reported at block 152.

After the relatively short timer period, three minutes being an example time, the system bath 14 temperature should have either reached the Command Zone or changed at least by the predetermined delta. If it has not, then the chiller/heater 26 is not functioning properly and an error will be reported.

The above test may be performed when the system is in "operate" or "standby". Also, no changes are made by the test to the patient target temperature set by the operator, and in the event that the operator changes target temperature, the test is delayed by an additional period (e.g., fifteen minutes) to allow the system to slew toward target temperature before testing it.

While the particular SYSTEM AND METHOD FOR TESTING HEAT EXCHANGE SYSTEM FOR HEAT EXCHANGE CATHETER is herein shown and described in detail, it is to be understood that the subject matter which is encompassed by the present invention is limited only by the claims.

What is claimed is:

1. A computer-implemented method for testing for proper functioning of a heat exchange system engageable with an indwelling heat exchange catheter to circulate working fluid therein using a pump, comprising:
    determining, using a digital processor, whether temperature of heat exchange fluid in a chamber through which the working fluid is circulated is within a range of a command temperature;
    if the temperature of the heat exchange fluid is not within the range, stopping the pump;
    receiving time input at the processor;
    using the time input to determine when a predetermined period commencing when the pump has stopped has elapsed; and
    only if (1) the temperature of the heat exchange fluid is not within the range at the elapse of the predetermined period after the pump has stopped, or (2) the temperature of the heat exchange fluid has not changed during the predetermined period after the pump has stopped by at least a predetermined amount, returning an error indication.

2. The method of claim 1, wherein if it is determined that the temperature is not within the range, deciding whether the temperature is warmer than the range or cooler than the range.

3. The method of claim 2, wherein if the temperature is warmer than the range the method further includes measuring the temperature with the pump stopped during the predetermined period and returning an error only at the elapse of the predetermined period if the temperature is not within the range or if the temperature has not changed during the predetermined period by at least the predetermined amount.

4. The method of claim 2, wherein if the temperature is cooler than the range the method further includes measuring the temperature with the pump stopped during the predetermined period and, if the temperature has not changed by the predetermined amount since the pump was stopped, determining whether a compressor has started.

5. The method of claim 4, comprising delaying the test if the compressor has not started.

6. A heat exchanger for treating working fluid to be circulated through an indwelling heat exchange catheter, comprising:
    a pump for pumping the working fluid in a fluid path;
    a heat exchange chamber in the path and containing a heat exchange fluid having a temperature; and
    at least one processor controlling the pump, the processor executing logic comprising:
    determining that the heat exchanger is not working properly if the temperature of the heat exchange fluid is not within an expected range only if (1) substantial equalization of heat exchange fluid temperature with working fluid temperature does not occur within a predetermined period after stopping the pump, or (2) temperature does not change by at least a predetermined amount within a predetermined period after stopping the pump.

7. The heat exchanger of claim 6, wherein if the temperature of the heat exchange fluid is not within the range, the processor stops the pump and only if (1) the temperature is not within the range at the elapse of the predetermined period, or (2) the temperature has not changed during the predetermined period by at least a predetermined amount, returns an error indication.

8. The heat exchanger of claim 7, wherein if it is determined that the temperature is not within the range, the processor decides whether the temperature is warmer than the range or cooler than the range.

9. The heat exchanger of claim 8, wherein if the temperature is warmer than the range the processor measures the temperature with the pump stopped during the predetermined period and returns an error only at the elapse of the predetermined period if the temperature is not within the range or if the temperature has not changed during the predetermined period by at least the predetermined amount.

10. The heat exchanger of claim 8, wherein if the temperature is cooler than the range the processor measures the temperature with the pump stopped during the predetermined period and, if the temperature has not changed by the predetermined amount since the pump was stopped, the processor determines whether a compressor has started.

11. The heat exchanger of claim 10, wherein the processor delays the test if the compressor has not started.

12. A processor for a heat exchange system for heating and cooling a working fluid circulated through a catheter by a pump, the processor programmed to execute logic comprising:
determining whether a fluid temperature is within a command zone range and if not, determining whether temperature moves toward the range or equalizes with it within predetermined parameters after a pump has stopped, and
only if temperature does not move toward the range or equalize with it within predetermined parameters after the pump has stopped, indicating an error, wherein if the temperature is cooler than the range the processor measures the temperature with the pump stopped during a predetermined period and, if the temperature has not changed by a predetermined amount since the pump was stopped, determines whether a compressor has started.

13. The processor of claim 12, wherein determining whether temperature moves toward the range or equalizes with it within predetermined parameters after a pump has stopped includes determining whether the temperature is within the range within the predetermined period after the pump is stopped, and determining whether the temperature has changed during the predetermined period by at least the predetermined amount.

14. The processor of claim 13, wherein if it is determined that the temperature is not within the range, the processor decides whether the temperature is warmer than the range or cooler than the range.

15. The processor of claim 14, wherein if the temperature is warmer than the range the processor measures the temperature with the pump stopped during the predetermined period and returns an error only at the elapse of the predetermined period if the temperature is not within the range or if the temperature has not changed during the predetermined period by at least the predetermined amount.

16. The processor of claim 2, wherein the processor delays the test if the compressor has not started.

\* \* \* \* \*